United States Patent [19]

Haardt et al.

[11] Patent Number: 5,560,367

[45] Date of Patent: Oct. 1, 1996

[54] METHOD FOR HIGH-RESOLUTION SPECTRAL ANALYSIS IN MULTI CHANNEL OBSERVATIONS USING A SINGULAR VALVE DECOMPOSITION (SVD) MATRIX TECHNIQUE

[75] Inventors: Martin Haardt, Munich; Peter Strobach, Roehrnbach, both of Germany

[73] Assignee: Siemens Aktiengesellschaft, Munich, Germany

[21] Appl. No.: 290,588

[22] Filed: Aug. 15, 1994

[30] Foreign Application Priority Data

Aug. 13, 1993 [EP] European Pat. Off. .............. 93113022

[51] Int. Cl.$^6$ ...................... A61B 5/0402; A61B 5/0472
[52] U.S. Cl. ...................... 128/702; 128/704; 364/413.06
[58] Field of Search .................................. 128/702, 704, 128/705, 695, 696; 364/413.02, 413.06

[56] References Cited

U.S. PATENT DOCUMENTS

| | | | |
|---|---|---|---|
| 4,974,162 | 11/1990 | Siegel et al. ............................. | 128/702 |
| 5,020,540 | 6/1991 | Chamoun ................................. | 128/702 |
| 5,109,862 | 5/1992 | Kelen et al. ............................. | 128/702 |
| 5,211,179 | 5/1993 | Haberl et al. ............................ | 128/702 |
| 5,215,099 | 6/1993 | Haberl et al. ............................ | 128/702 |
| 5,341,811 | 8/1994 | Cano ....................................... | 128/696 |
| 5,348,020 | 9/1994 | Hutson ..................................... | 128/696 |
| 5,490,516 | 2/1996 | Hutson ..................................... | 128/696 |

FOREIGN PATENT DOCUMENTS

| | | | |
|---|---|---|---|
| 1194391 | 11/1985 | U.S.S.R. ................................. | 128/696 |
| WO93/03544 | 2/1993 | WIPO . | |

OTHER PUBLICATIONS

"The Detection, Significance and Effect of Drugs upon Ventricular Late Potentials," Balderson et al., Auomedica, 1991 vol. 13, pp. 67–96.

"An Introduction to High–Resolution ECG Recordings of Cardiac Late Potentials," Berbari et al., Arch. Intern. Med., vol. 148, Aug. 1988, pp. 1859–1863.

"Spectrum Analysis –A Modern Perspective," Kay et al., Proceedings of the IEEE, vol. 69, No. 11, Nov. 1981, pp. 1380–1419.

"Model Based Processing of Signals: A State Space Approach," Rao et al., Proceedings of the IEEE, vol. 80, No. 2, Feb. 1992, pp. 283–309.

"Detection of Signals by Information Theoretic Criteria," Wax et al., IEEE Trans. on Acoust., Speech and Sig. Proces., vol. ASSP-33, No. 2, Apr. 1985, pp. 387–392.

"Cardiac Micropotentials Reached From One Systole as Non-dipolar Residue by Singular Value Decomposition," DRška et al., Physiol. Res., vol. 42, 1993, pp. 73–76.

*Primary Examiner*—William E. Kamm
*Assistant Examiner*—Carl H. Layno
*Attorney, Agent, or Firm*—Hill, Steadman & Simpson

[57] ABSTRACT

A method for high-resolution spectral analysis in multi-channel observations is disclosed with which it is possible to detect ventricular late potentials in individual heartbeats. The method also offers the basis for the spatial localization of pathological tissue modification that has a cause-and-effect relationship to the creation of these late potentials. The applicability of the method of the invention can be similarly applied to problems in radar or sonar technology, astronomy, measuring mobile radio telephone channels or to other problems of seismic or medical signal processing.

45 Claims, 3 Drawing Sheets

METHOD FOR HIGH-RESOLUTION SPECTRAL ANALYSIS IN MULTI CHANNEL OBSERVATIONS USING A SINGULAR VALVE DECOMPOSITION (SVD) MATRIX TECHNIQUE

BACKGROUND OF THE INVENTION

1. Field of the Invention

The invention is directed to a method for high-resolution spectral analysis wherein signals are obtained in multiple channels. The invention is also directed to the employment of such a method for the detection of ventricular late potentials in multi-channel measuring methods in medical technology wherein signals derived from the heart are evaluated, such as magnetocardiography (MCG) or electrocardiography (ECG).

2. Description of the Prior Art

Methods for spectral analysis are required in order to find and in order to identify possibly attenuated, harmonic parts in signals with a large variety of origins.

Known methods for spectral analysis and their employment in the context of the identification of late potentials have been disclosed in the publications by D. E. Balderson, et al., "The Detection, Significance and Effect of Drugs upon Ventricular Late Potentials", Automedia, vol. 13, pp. 67–96, 1991 and E. J. Berbari et al., "An Introduction to High-Resolution ECG Recordings of Cardiac Late Potentials", Arch. Intern. med., vol. 148, pp. 1859–1863, August 1988. Further, the articles by S. M. Kay et al., "Spectrum Analysis—A Modern Perspective", Proceedings of the IEEE, Vol. 69, No. 11, November 1981, B. D. Rao et al., "Model based Processing of Signals: A State Space Approach", Proc. IEEE, vol. 80 pp. 283–309, Feb. 1992 and S. Haykin, Editor, "Nonlinear Methods of Spectral Analysis", Topics in Applied Physics, vol. 34, Springer-Verlag, 1979 provide a good survey of the known methods for spectral analysis.

These known methods have certain strengths and weaknesses. No known method, however, makes it possible to document ventricular late potentials in individual heartbeats employing multi-channel measured data.

SUMMARY OF THE INVENTION

An object of the invention is to specify a method for high-resolution spectral analysis in multi-channel observations with which ventricle late potentials can be detected in individual heartbeats.

The above object is achieved in accordance with the principles of the present invention in a method wherein data are obtained from a subject using a plurality of sensors, the respective sensor signals being combined to form a data vector, and a plurality of data vectors are combined to form a matrix. A singular value resolution is implemented by a threshold operation, wherein all elements of the matrix which are lower than the threshold are replaced by zero. This resolved matrix is used to identify matrices $\Theta_1$ and $\Theta_2$, and a matrix F is identified as the optimum solution to the over-defined equation system $\Theta_1 \cdot F = \Theta_2$. The imaginary parts of the natural logarithms of the eigenvalues of F are the soft, spectral frequencies, and the real parts of the natural logarithms of the eigenvalues of F are attenuation constants for these frequencies. A frequency histogram can then be generated, from which late potentials can be identified.

The method makes the detection of ventricular late potentials in individual heartbeats possible. The method also offers the possibility of spacial localization of pathological modifications that have a cause-and-effect relationship with the creation of these late potentials. This method has the noteworthy advantage of being entirely independent of the geometry of the sensor field employed.

DESCRIPTION OF THE PREFERRED EMBODIMENTS

The invention constitutes a new, high-resolution method for estimating a plurality of superimposed, possibly attenuated, exponential oscillations from multi-channel, noisy observations. The solution of the invention is based on a state analysis of the measured signals, as a result of which the non-linear estimation problem is linearly parameterized. It is noteworthy that the method is independent of the spatial arrangement of the sensors employed for collecting the measured data and it can therefore be applied given an arbitrary, geometry of the sensor field, and can thus be used both in circumstance wherein the geometry is known (predetermined) or unknown.

The applicability of the method of the invention is not limited to the detection of ventricular late potentials, but can be similarly applied to problems of radar or sonar technology, astronomy, measuring mobile radio telephone channels or to other problems of seismic or medical signal processing.

In order to mathematically describe the spectral estimation problem, it is assumed that M sensors receive the sum of p possibly attenuated exponential oscillations. When the signal observed at the $i_{th}$ sensor ($1 \leq i \leq M$) at a time n (with $0 \leq n \leq L-1$) is called $y_i(n)$, the noise-free observations can be described in the following way:

$$y_i(n) = \sum_{v=1}^{p} c_{v,i} \cdot \lambda_v^n = \sum_{v=1}^{p} c_{v,i} \cdot e^{(\gamma_v + j\omega_v)n}$$

The unknown, complex amplitude of the $v_{th}$ exponential oscillation in the $i_{th}$ channel as thereby referenced $c_{v,i}$, and $\gamma_v$ can be interpreted as the attenuation and $\omega_v$ as the frequency of the $v_{th}$ exponential oscillation. Obviously, real signals can also be handled since real harmonic oscillations can be presented as the sum of two (complex) exponential oscillations.

Subsequently, the observations at the M sensors are combined to form a data vector $$y(n) = [(y_1(n), \ldots, y_M(n)]^T$$

The following notation is thereby employed: column vectors and matrices are identified by bold face lower case or upper case letters. Transposed and complex-conjugate transparent matrices and vectors are respectively designated with T or H.

Figure 1:
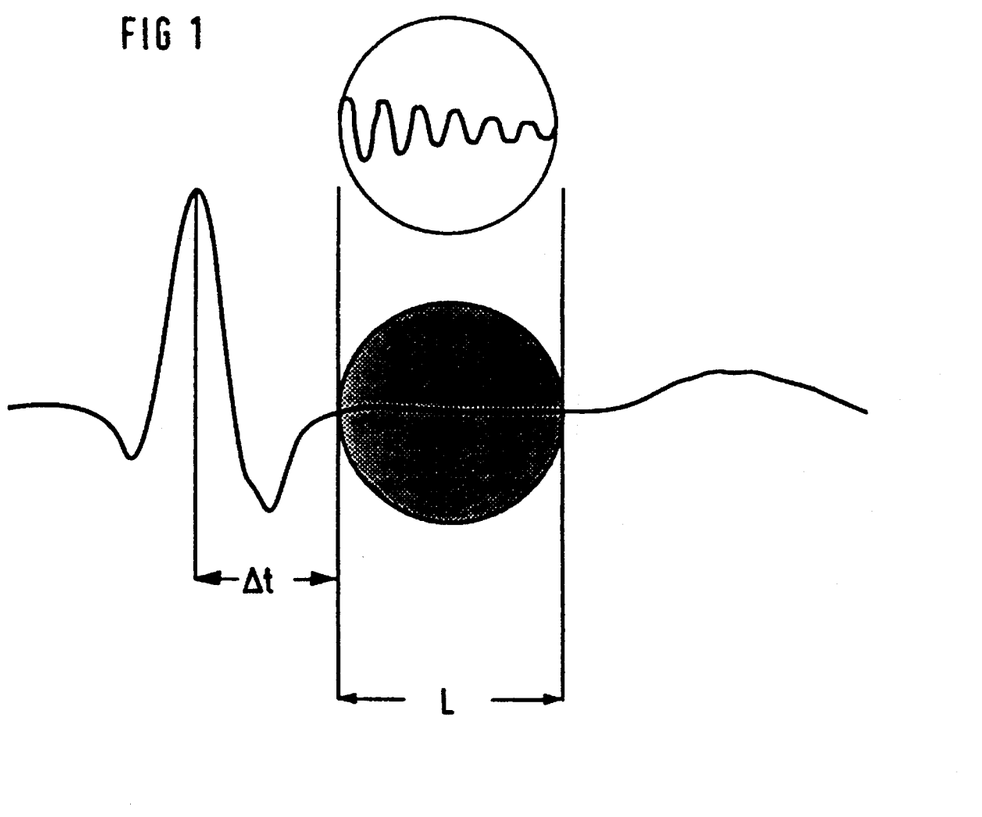
FIG. 1 is a schematic illustration of the chronological curve of a heartbeat signal, specifically the QRS complex and the ST distance following thereupon.

Ventricular late potentials are high-frequency signals having low amplitudes in the terminal part of the QRS complex and in the ST distance or: path of the heartbeat (see FIG. 1). These pathological signal parts correspond to a locally retarded tissue excitation spread ensuing at intervals. Such late potentials are often identified in patients having ventricular tachycardia. Their significance for diagnosis lies especially in the risk evaluation of patients having ventricular arrhythmia and in designing the therapy therefor or for therapy monitoring. The method of the invention supplies a suitable method for detecting late potentials from a multi-channel series of measurements.

Late potentials can be documented in an electrocardiogram (ECG) as well as in a magnetocardiogram (MCG), whereby the same method can be fundamentally applied given both types of measurement. Differing from ECG, however, far more channels, typically up to 37 simultaneously registered measurement channels, are available given biomagnetic (MCG) measurements. Since the measured data in these channels are correlated to a high degree, they offer the precondition for a substantially more reliable detection of the late potentials than given single-channel measuring methods.

Heretofore, late potentials were identified with the assistance of signal averaging techniques, or with the assistance of a frequency analysis based on fast Fourier transformation. These; methods, however, are not suitable for detecting ventricular late potentials in individual heartbeats.

The method of the invention can be implemented in two versions that are based on two different state presentations of the signals: the first version of the method of the invention proceeds on the basis of what is referred to as expanded state presentation of the signals. In each version measured data, such as ECG signals or MCG signals, are obtained from a subject in a known manner. The measured data are presented in the form of a matrix $$Y_E = \begin{bmatrix} y^T(0) & y^T(1) & \ldots & y^T(N-L) \\ y^T(1) & y^T(2) & \cdots & y^T(N-L+1) \\ \cdot & \cdot & & \cdot \\ \cdot & \cdot & & \cdot \\ y^T(L-1) & y^T(L) & \cdots & y^T(N-1) \end{bmatrix}$$

by contrast whereto the other version of the method of the invention proceeds on the basis of what is referred to as traditional status presentation, represented by the matrix $$Y_T = \begin{bmatrix} y(0) & y(1) & \ldots & y(N-L) \\ y(1) & y(2) & \ldots & y(N-L+1) \\ \cdot & \cdot & & \cdot \\ \cdot & \cdot & & \cdot \\ y(L-1) & y(L) & \ldots & y(N-1) \end{bmatrix}$$

The two presentations are mathematical equivalent but have formally different properties. Dependent on the values of the parameters N, M and L, the user of the method of the invention selects that presentation from the two fundamentally equivalent alternatives which leads to an optimally quadratic matrix, i.e. a matrix having an optimally small difference between row and column number. Such a selection leads to optimum numerical properties in the implementation of the method of the invention.

The individual method steps for the implementation of the method of the invention shall be set forth in detail below using the above-recited notation.

A first version of the method of the invention for high-resolution spectral analysis is as follows:

a) M chronological sequences $y_i(n)$ of measured data of the sensor channels $1 \leq i \leq M$ are observed at the times $0 \leq n \leq N-1$ and are combined to form a matrix $\gamma_E$ having the form $$Y_E = \begin{bmatrix} y^T(0) & y^T(1) & \ldots & y^T(N-L) \\ y^T(1) & y^T(2) & \cdots & y^T(N-L+1) \\ \cdot & \cdot & & \cdot \\ \cdot & \cdot & & \cdot \\ y^T(L-1) & y^T(L) & \cdots & y^T(N-1) \end{bmatrix}$$

with $y(n) = [y_1(n), \ldots, y_M(n)]^T$.

b) A singular value resolution $\gamma_E = U \cdot \Sigma \cdot V^H$ of the matrix $\gamma_E$ is implemented and the singular values are subjected to a threshold operation, as a result of which all singular values of $\gamma_E$ that are lower than the threshold in terms of amount are replaced by zero and in accord wherewith all p dominant singular values, i.e. all singular values of $\gamma_E$ not replaced by zero are contained in the block matrix $\Sigma_1$ of the resolution $$Y_E = [U_1 \; U_2] \cdot \begin{bmatrix} \Sigma_1 & 0 \\ 0 & 0 \end{bmatrix} \cdot \begin{bmatrix} V_1^H \\ V_2^H \end{bmatrix}$$

c) those matrices $\Theta_1$ and $\Theta_2$ are identified for which $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

is valid, whereby $\Theta_1$ and $\Theta_2$ respectively indicate the first and the last block matrix.

d) a matrix F is identified which is an optimum solution of the generally over-defined equation system $\Theta_1 \cdot F = \Theta_2$, whereby the imaginary parts of the natural logarithms of the eigenvalues of F are the soft, spectral frequencies, and the real parts of the natural logarithms of the eigenvalues of F are attenuation constants associated with these frequencies.

This first version of the inventive method is thus a method for high-resolution spectral analysis wherein M chronological sequences $y_i(n)$ of measured data of the sensor channels $1 \leq i \leq M$ are observed at the times $0 \leq n \leq N-1$, wherein spectral frequencies and attenuation constants associated with these frequencies are respectively identified as imaginary parts or real parts of the natural logarithms of the eigenvalues of a matrix F that is defined as the optimum solution of a generally over-defined equation system $\Theta_1 \cdot F = \Theta_2$, whereby the matrices $\Theta_1$ and $\Theta_2$ are defined by the relationship $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

wherein $\theta_1$ and $\theta_2$ respectively identify the first or, respectively, the last block matrix and wherein the matrices $\Sigma_1$ and $U_1$ are defined by the approximate singular value resolution $$Y_E = [U_1 \; U_2] \cdot \begin{bmatrix} \Sigma_1 & 0 \\ 0 & 0 \end{bmatrix} \cdot \begin{bmatrix} V_1^H \\ V_2^H \end{bmatrix}$$

of a matrix $$Y_E = \begin{bmatrix} y^T(0) & y^T(1) & \ldots & y^T(N-L) \\ y^T(1) & y^T(2) & \ldots & y^T(N-L+1) \\ \cdot & \cdot & & \cdot \\ \cdot & \cdot & & \cdot \\ \cdot & \cdot & & \cdot \\ y^T(L-1) & y^T(L) & \ldots & y^T(N-1) \end{bmatrix}$$

whereby $y(n)=[y_1(n), \ldots, y_M(n)]^T$.

Thus an approximate singular resolution is identified from an original singular value resolution $\gamma_E = U \cdot \Sigma \cdot V^H$ in that the singular values are subjected to a threshold operation, as a result of which all singular values of $\gamma_E$ that are smaller in amount than the threshold are replaced by zero and all p dominant singular values of $\gamma_E$, i.e., singular values of $\gamma_E$ not replaced by zero are contained in the block matrix $\Sigma_1$ of the approximate resolution.

This first version of the method of the invention is based on what is referred to as expanded state presentation. This version is accessible to an expansion, which shall be set forth later, and with which the precision of the spectral analysis can be improved further given the absence of attenuation phenomena (disappearing attenuation constant).

A fundamentally equivalent, but formally different, second version of the method of the invention for high-resolution spectral analysis is as follows:

a) M chronological sequences $y_i(n)$ of measured data of the sensor channels $1 \leq i \leq M$ are observed at the times $0 \leq n \leq N-1$ and are combined to form a matrix $\gamma_T$ having the form $$Y_T = \begin{bmatrix} y(0) & y(1) & \ldots & y(N-L) \\ y(1) & y(2) & \ldots & y(N-L+1) \\ \cdot & \cdot & & \cdot \\ \cdot & \cdot & & \cdot \\ \cdot & \cdot & & \cdot \\ y(L-1) & y(L) & \ldots & y(N-1) \end{bmatrix}$$

with $y(n)=[y_1(n), \ldots, y_M(n)]^T$.

b) A singular value resolution $Y_T = U \cdot \Sigma \cdot V_H$ of the matrix $\gamma_T$ is implemented and the singular values are subjected to a threshold operation, as a result of which all singular values (elements) of $Y_T$ that are lower than the threshold in terms of amount are replaced by zero and in accord wherewith all p dominant singular values, i.e. all singular values of $Y_T$ not replaced by zero are contained in the block matrix $\Sigma_1$ of the resolution $$Y_T = [U_1 \ U_2] \cdot \begin{bmatrix} \Sigma_1 & 0 \\ 0 & 0 \end{bmatrix} \cdot \begin{bmatrix} V_1^H \\ V_2^H \end{bmatrix}$$

c) those matrices $\theta_1$ and $\theta_2$ are identified for which $$U_1 \cdot \Sigma_1^{1/2} = \begin{bmatrix} \Theta_1 \\ \Theta_2 \end{bmatrix} = \begin{bmatrix} \theta_1 \\ \Theta_2 \end{bmatrix}$$

is valid, whereby $\theta_1$ and $\theta_2$ respectively indicate the first and the last block matrix.

d) a matrix F is identified which is an optimum solution of the generally over-defined equation system $\theta_1 \cdot F = \theta_2$, whereby the imaginary parts of the natural logarithms of the eigenvalues of F are the soft, spectral frequencies, and the real parts of the natural logarithms of the eigenvalues of F are attenuation constants associated with these frequencies.

This second version of the inventive method is thus a method for high-resolution spectral analysis wherein M chronological sequences $y_i(n)$ of measured data of the sensor channels $1 \leq i \leq M$ are observed at the times $0 \leq n \leq N-1$, wherein spectral frequencies and attenuation constants associated with these frequencies are respectively identified as imaginary parts or real parts of the natural logarithms of the eigenvalues of a matrix F that is defined as the optimum solution of a generally over-defined equation system $\theta_1 \cdot F = \theta_2$, whereby the matrices $\theta_1$ and $\theta_2$ are defined by the relationship $$U_1 \cdot \Sigma_1^{1/2} = \begin{bmatrix} \Theta_1 \\ \Theta_2 \end{bmatrix} = \begin{bmatrix} \theta_1 \\ \Theta_2 \end{bmatrix}$$

wherein $\theta_1$ and $\theta_2$ respectively identify the first or the last block matrix and wherein the matrices $\Sigma_1$ and $U_1$ are defined by the approximate singular value resolution $$Y_T = [U_1 \ U_2] \cdot \begin{bmatrix} \Sigma_1 & 0 \\ 0 & 0 \end{bmatrix} \cdot \begin{bmatrix} V_1^H \\ V_2^H \end{bmatrix}$$

of a matrix $$Y_T = \begin{bmatrix} y(0) & y(1) & \ldots & y(N-L) \\ y(1) & y(2) & \ldots & y(N-L+1) \\ \cdot & \cdot & & \cdot \\ \cdot & \cdot & & \cdot \\ \cdot & \cdot & & \cdot \\ y(L-1) & y(L) & \ldots & y(N-1) \end{bmatrix}$$

whereby $y(n)=[y_1(n), \ldots, y_M(n)]^T$.

Thus an approximate singular resolution is identified from an original singular value resolution $Y_T = U \cdot \Sigma \cdot V^H$ in that the singular values are subjected to a threshold operation, as a result of which all singular values of $Y_T$ that are smaller in amount than the threshold are replaced by zero and all p dominant singular values of $Y_T$, i.e., singular values of $Y_T$ not replaced by zero are contained in the block matrix $\Sigma_1$ of the approximate resolution.

This second version of the method of the invention is based on what is referred to as conventional state presentation.

Figure 3:
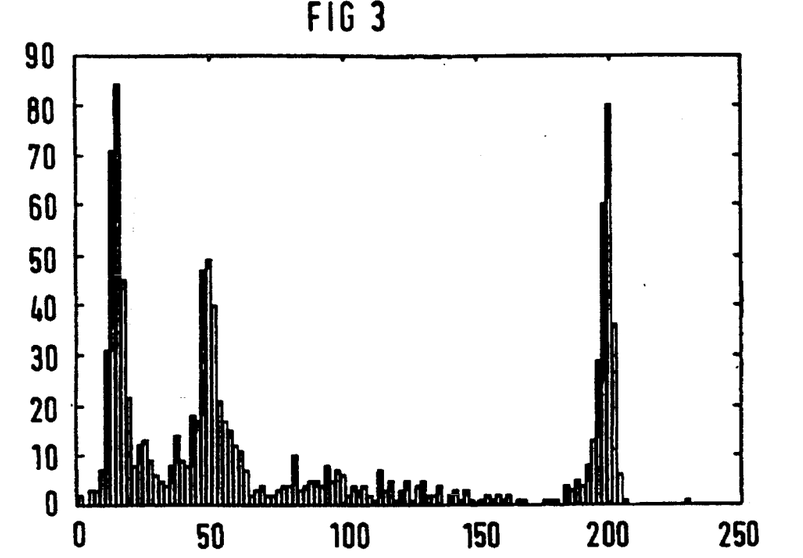
FIGS. 3 and 4 show frequency histograms of patients having late potentials identified with the method of the invention wherein the number of found frequencies (ordinate) is entered over the frequency in Hertz (abscissa).
Figure 4:
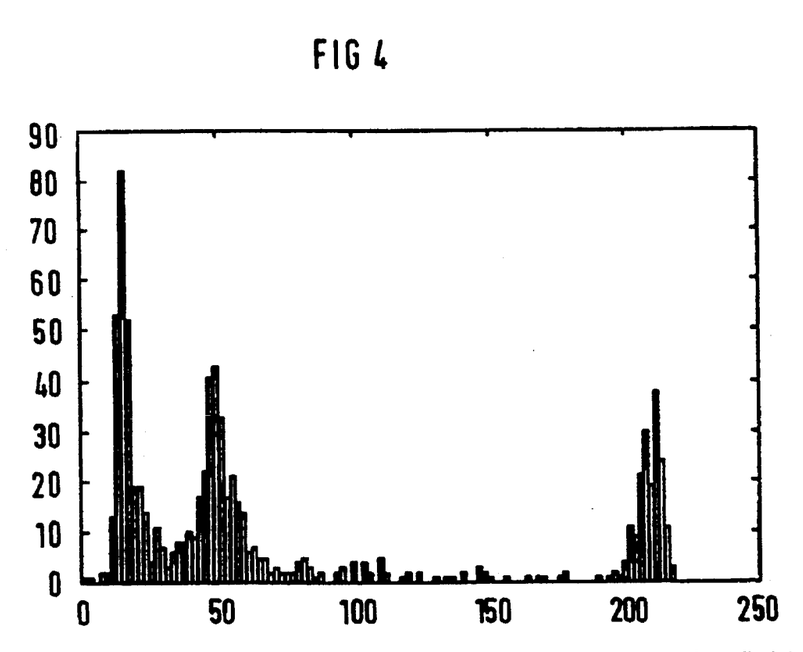
Figure 5:
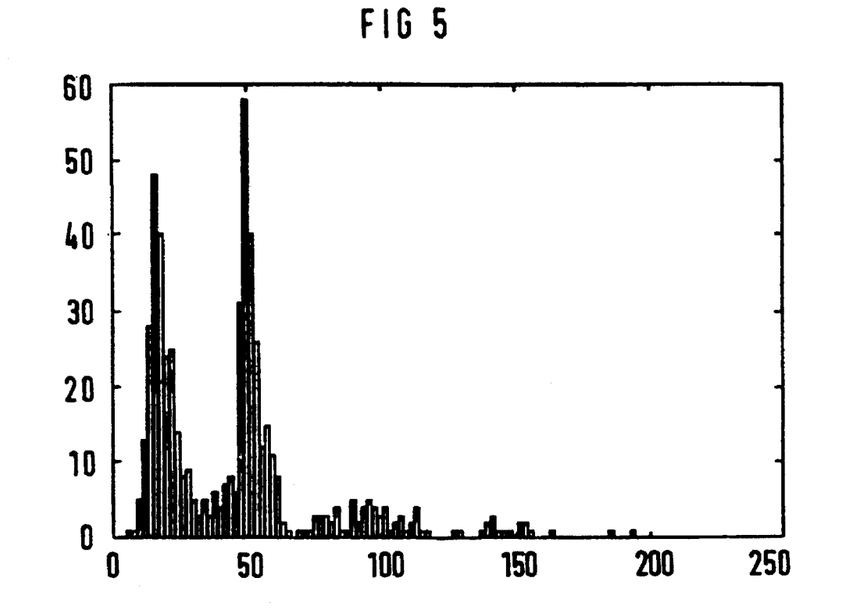
FIGS. 5 and 6 show frequency histograms of patients without late potentials identified with the method of the invention wherein the number of found frequencies (ordinate) is entered over the frequency in Hertz (abscissa).
Figure 6:
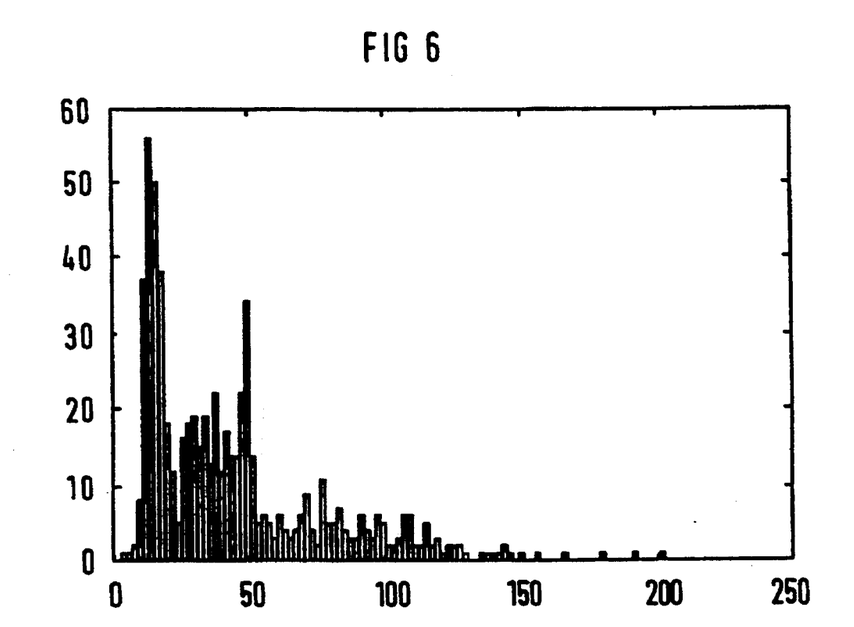

Two versions of the method for the invention for identifying spectral frequencies and attenuation constants associated with these spectral frequencies have thus been described. FIGS. 3, 4, 5 and 6 schematically show various frequency histograms that were calculated with the method of the invention. FIGS. 3 and 4 show frequency histograms of patients having late potentials. These are easily recognized based on the accumulation of high frequency components around approximately 200 Hertz. In FIGS. 5 and 6, which show frequency histograms of subjects without late potentials, these accumulations at the upper end of the spectrum are lacking.

In some instances, however, the user is interested not only in the frequencies and attenuation constants but also in the amplitudes and phases of the spectral oscillations. These can be calculated from complex value amplitudes of these oscillations any way familiar to a person skilled in the art.

A preferred embodiment of the invention in a method according to the above-described first version is therefore characterized in the calculation of the matrix C of the complex value amplitudes $c_{j,i}$ of the oscillations associated with the spectral frequencies $j=1, \ldots, p$ in the sensor channel $i=1, \ldots, M$ the implementation of the following steps:

a) proceeding from the similarity transformation $F = S \cdot \Lambda \cdot S^{-1}$ of the matrix F and the diagonal form $\Lambda$ thereof, the matrices $U_1 \cdot \theta_1^{1/2} \cdot S$ and $S^{-1} \cdot \theta_1^{1/2} \cdot V_1^H$ are formed and are subdivided into block matrices $$U_1 \cdot \Sigma_1^{1/2} \cdot S = \begin{bmatrix} V_1^T \\ V_2^T \\ V_3^T \\ \cdot \\ \cdot \\ \cdot \\ V_L^T \end{bmatrix} \text{ as well as}$$

$$S^{-1} \cdot \Sigma_1^{1/2} \cdot V_1^H = [W_1 \; W_2 \; W_3 \ldots W_{N-L+1}]$$

b) the matrices $$\begin{bmatrix} V_1^T \\ V_2^T \cdot \Lambda^{-1} \\ V_3^T \cdot \Lambda^{-2} \\ \cdot \\ \cdot \\ \cdot \\ V_L^T \cdot \Lambda^{-(L-1)} \end{bmatrix} \text{ and } [W_1 \Lambda^{-1} \cdot W_2 \Lambda^{-2} \cdot W_3 \ldots \Lambda^{-(N-L)} \cdot W_{N-L+1}]$$

are derived from the matrices of step (a).

$$\begin{bmatrix} V_1^T \\ V_2^T \cdot \Lambda^{-1} \\ V_3^T \cdot \Lambda^{-2} \\ \cdot \\ \cdot \\ \cdot \\ V_L^T \cdot \Lambda^{-(L-1)} \end{bmatrix}$$

c) the matrix C of the complex amplitudes is then calculated according to the relationship $C=\text{diag}\{h_1, h_2, \ldots, h_p\} \cdot X_D$, whereby $h^T=(h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \cdot \\ \cdot \\ \cdot \\ V_L^T \cdot \Lambda^{-(L-1)} \end{bmatrix}$$

and $X_D$ indicates the average value of the block matrices in $$[W_1 \Lambda^{-1} \cdot W_2 \Lambda^{-2} \cdot W_3 \ldots \Lambda^{-(N-L)} \cdot W_{N-L+1}].$$

A corresponding development of the above-described, second version of the method of the invention is equivalent thereto, this being characterized in that the matrix C of the complex-value amplitudes $c_{j,i}$ of the oscillations associated with the spectral frequencies $j=1, \ldots, p$ in the sensor channel $i=1, \ldots, M$ is calculated by implementing the following steps:

a) proceeding from the similarity transformation $F = S \cdot \Lambda \cdot S^{-1}$ of the matrix F and the diagonal form $\Lambda$ thereof, the matrices $U_1 \cdot \Sigma_1^{1/2} \cdot S$ and $S^{-1} \cdot \Sigma_1^{1/2} \cdot V_1^H$ are formed and are subdivided into block matrices $$U_1 \cdot \Sigma_1^{1/2} \cdot S = \begin{bmatrix} V_1^T \\ V_2^T \\ V_3^T \\ \cdot \\ \cdot \\ \cdot \\ V_L^T \end{bmatrix} \text{ as well as}$$

$$S^{-1} \cdot \Sigma_1^{1/2} \cdot V_1^H = [W_1 \; W_2 \; W_3 \ldots W_{N-L+1}]$$

b) the matrices $$\begin{bmatrix} V_1^T \\ V_2^T \cdot \Lambda^{-1} \\ V_3^T \cdot \Lambda^{-2} \\ \cdot \\ \cdot \\ \cdot \\ V_L^T \cdot \Lambda^{-(L-1)} \end{bmatrix} \text{ and } [W_1 \Lambda^{-1} \cdot W_2 \Lambda^{-2} \cdot W_3 \ldots \Lambda^{-(N-L)} \cdot W_{N-L+1}]$$

are derived from the matrices of step (a).

c) the matrix C of the complex amplitudes is then calculated according to the relationship $C^T = H_D \cdot \text{diag}\{x_1, x_2, \ldots, x_p\}$ whereby $x=[x_1, x_2, \ldots, x_p]^T$ references the average value of the column vectors of $[W_1 \Lambda^{-1} \cdot W_2 \Lambda^{-2} \cdot W_3 \ldots \Lambda^{-(N-L)} \cdot W_{N-L+1}]$ and $H_D$ in indicates the average value of the block matrices in $$\begin{bmatrix} V_1^T \\ V_2^T \cdot \Lambda^{-1} \\ V_3^T \cdot \Lambda^{-2} \\ \cdot \\ \cdot \\ \cdot \\ V_L^T \cdot \Lambda^{-(L-1)} \end{bmatrix}$$

The real oscillation amplitudes and the associated phases can be easily identified from the complex-value amplitudes of the spectral frequencies. Given a known geometry of the sensor field, the observed signals freed of measuring errors can be reconstructed from these values and can be presented at a suitable output means, for example at a monitor. The location of the origin of specific signal parts can be reconstructed very exactly from the phases of the oscillations and there shifts between the individual sensors. As a result, for example, it is possible to identify the originating location of a pathological signal part from a single QRS complex of a single heartbeat in the myocardium.

It is especially advantageous in all described versions of the method to calculate the matrix F with the assistance of the method of the least error squares or with the assistance of the method of the least total error squares (total least squares). The generally known mathematical literature for engineers provides a person skilled in the art with the necessary instruction to accomplish this.

The complex amplitudes and eigenvalues estimates with the assistance of the method of the invention are substantially more precise than the values calculated with known methods for, spectral analysis. The estimation results of the method of the invention, further, are extremely resistant to noise signals that can be superimposed on the measured signals, namely because of the numerically extremely stable mathematical methods such as, for example, singular value resolution and eigenvalue resolution.

The expanded state presentation offers a possibility in the case of unattenuated exponential oscillations (disappearing attenuation constants) to additionally improve the estimation precision. Unattenuated exponential oscillations are characterized by disappearing real parts of the logarithmized eigenvalues of the matrix F. In this case, an expanded block-Hankel matrix $$\begin{bmatrix} y^T(0) & y^T(1) & \ldots & y^T(N-L) & y^H(0) & y^H(1) & \ldots & y^H(N-L) \\ y^T(1) & y^T(2) & \cdots & y^T(N-L+1) & y^H(1) & y^H(2) & \cdots & y^H(N-L+1) \\ \cdot & \cdot & & \cdot & \cdot & \cdot & & \cdot \\ \cdot & \cdot & & \cdot & \cdot & \cdot & & \cdot \\ \cdot & \cdot & & \cdot & \cdot & \cdot & & \cdot \\ y^T(L-1) & y^T(L) & \cdots & y^T(N-L) & y^H(L-1) & y^H(L) & \cdots & y^H(N-1) \end{bmatrix}$$

can be introduced, replacing the matrix $\gamma_E$. When this matrix is employed instead of the matrix $\gamma_E$, estimates for the frequencies, attenuation constants, amplitudes and phases of the harmonic parts in the measured data are obtained with a precision comparable to the precision that is achieved given linear prediction problems by simultaneous combination of forward and backward prediction. In this case, it is also appropriate to solve the over-defined equation system for calculating the matrix F with the assistance of an optimization method using secondary conditions which assure that the logarithmized eigenvalues of the matrix F have real parts approaching zero. In this way, one obtains a unitary matrix F whose logarithmized eigenvalues, as desired, are automatically purely imaginary.

Figure 2:
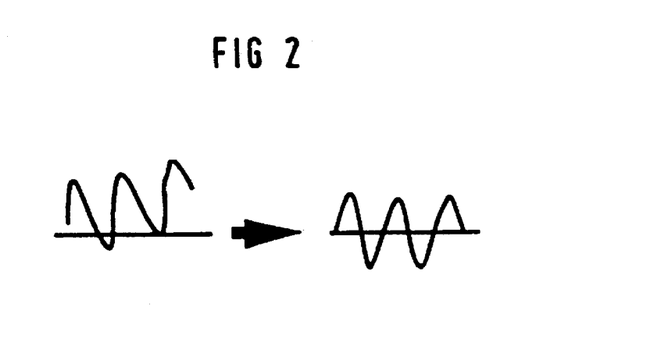
FIG. 2 is a schematic illustration of the compensation of a constant part and of a linear trend in the measured signal.

The method of the invention for spectral analysis can then be applied for the identification of ventricle late potentials in multi-channel MCG or ECG data. This employment utilizes the heartbeat as the trigger for the extraction of a relevant data interval, whose window is presented as in FIG. 1, that is located in the terminal part of the QRS complex. In a further step of pre-processing, it is often appropriate to eliminate constant parts and linear trends in the measured signals using known pre-processing methods. For the compensation of constant parts and liner trends, for example, a straight line can be matched to the measured data and this can be subsequently subtracted from the measured data. This compensation of the constant parts and linear trends is schematically shown in FIG. 2. These pre-processing steps are then followed by the actual high-resolution spectral analysis, as already presented above.

FIG. 1 shows a typical curve of the human heartbeat. A person skilled in the art has a number of known methods available to him for triggering the maximum of the QRS complex. In an especially suitable method for this is disclosed in the PCT WO 92/00539. The parameters of delay $\Delta t$ and window length L defined in FIG. 1 can be freely selected (for example, by the physician). In the first step of the method of the invention, the data excerpt which lies in the region identified by the parameter L (window length) is extracted from all M observed channels.

Subsequently, the extracted data excerpts are approximated by a straight line in each channel, for example with matching by minimization of the sum of the error squares. The estimated straight lines are subsequently subtracted from the extracted raw data. As a result of this procedure, possibly existing constant parts and potentially existing linear trends are compensated in all M channels (see FIG. 2).

The modeling of the heart signal in the extracted data interval as a superimposition of possibly attenuated, sinusoidal oscillations corresponds to an estimate of the harmonic signal parts in the post-QRS region of the heartbeat.

The inventive method for high-resolution multi-channel spectral analysis already set forth in detail has proven especially suitable for this application, since, as experiments have shown, all M sensors of the measuring structure register the same frequencies but the amplitudes of theses oscillations as well as the phases of these oscillations can be different at all channels.

In order to be able to identify the dominant singular values in the singular value resolution of the block matrices Y, it is expedient to apply a criterion that is independent from the energy of the individual heartbeat. To this end, the singular values are squared and these squares are normed to the sum of all squared singular values. The relative energy coefficients identified in this way are compared to a predetermined threshold. This predetermined threshold can be determined with various statistical methods for signal detection as presented in detail, for example, in the article by M. Wax et al. "Detection of Signals by Information Theoretic Criteria", IEEE Trans. Acoust., Speech, Signal Processing, vol. ASSP-33, pp. 387–392, April 1985. It is also expedient to select the threshold such that an even-numbered plurality of dominant singular values derives, since every real sinusoidal oscillation, as known, is the sum of two complex exponential oscillations.

In order to be able to visually evaluate the results of the spectral analysis method in a comfortable way, it is expedient to combine the estimated harmonic signal parts for every analyzed heartbeat by superimposition to form a synthetic heartbeat signal and to display this synthetic signal in a suitable way using conventional output devices. This measure is in fact not absolutely necessary but enables a comfortable optical evaluation of the estimation results. In this way, late potentials can be localized both spatially as well as chronologically in the individual heartbeat.

The method of the invention was extensively tested on the basis of magnetocardiographic data sets. The histograms shown in FIGS. 3–6 show the dominant frequencies found in four different data sets. The number of the found frequencies is thereby shown in a frequency interval over the frequency measured in the heart. The retardation $\Delta t$ thereby amounted to 50 ms, the window length L amounted to 90 ms. Thirty measuring channels working parallel were evaluated. Clear signal parts in the range of 15 Hz, corresponding to the decay of the QRS complex, and in the region of 50 Hz, corresponding to the mains frequency, occurred in the case of all four patients. Given patients having late potentials, an accumulation of harmonic signal parts around approximately 200 Hz can be additionally clearly recognized (see FIGS. 3 and 4). This accumulation in the upper frequency ranges is not present given healthy subjects (see FIGS. 4 and 5). Due to the presentation of the found frequencies in histogram form, late potentials can therefore be very easily diagnosed.

After the attending physician has analyzed the frequency histogram of a patient, the frequencies in the data set of interest to him or her can be viewed, for example on the basis of the synthetic signal. As a result, a chronological localization of the late potentials, i.e., the specifics regarding what late potentials appeared in what individual heartbeat, is possible. Further, a spatial localization of the late potentials is possible by evaluating the amplitudes and phases in the M sensor channels.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for high-resolution spectral analysis of electrical cardiac signals comprising the steps of:

(a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ in said plurality i of sensor channels with $1 \leq i \leq M$ at times n with $0 \leq n \leq N-1$;

(b) combining said cardiac sequences $y_i(n)$ to form a data vector and transposing said data vector to obtain $$y(n) = [(y_1(n), \ldots, y_m(n)]^T$$

(c) combining a plurality of data vectors $y_n$ to form a matrix $$Y_E = \begin{bmatrix} y^T(0) & y^T(1) & \cdots & y^T(N-L) \\ y^T(1) & y^T(2) & \cdots & y^T(N-L+1) \\ \cdot & \cdot & & \cdot \\ \cdot & \cdot & & \cdot \\ y^T(L-1) & y^T(L) & \cdots & y^T(N-1) \end{bmatrix}$$

(d) implementing a singular value resolution $\gamma_E = U \cdot \Sigma \cdot V_H$ of the matrix $\gamma_E$ and the singular values are subjected to a threshold operation, as a result of which all singular values of $\gamma_E$ that are lower than the threshold in terms of amount are replaced by zero and all singular values of $\gamma_E$ not replaced by zero are contained in the block matrix $\Sigma_1$ of the resolution $$Y_E = [U_1\ U_2] \cdot \begin{bmatrix} \Sigma_1 & 0 \\ 0 & 0 \end{bmatrix} \cdot \begin{bmatrix} V_1^H \\ V_2^H \end{bmatrix}$$

(e) identifying matrices $\theta_1$ and $\theta_2$ for which $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

whereby $\theta_1$ and $\theta_2$ respectively indicate the first and the last block matrix; and (f) identifying a matrix F which is an optimum solution of the generally over-defined equation system $\theta_1 \cdot F = \theta_2$, wherein the imaginary parts of the natural logarithms of the eigenvalues of F are the soft, spectral frequencies of said cardiac sequences $y_1(n)$, and the real parts of the natural logarithms of the eigenvalues of F are attenuation constants associated with these frequencies, and identifying a location in said subject of a source of selected parts of said cardiac sequences $y_1(n)$ from said complex amplitude on the basis of said known spatial arrangement of said sensors.

2. A method as claimed in claim 1 comprising the additional steps of:

(g) from the similarity transformation $F = S \cdot \Lambda \cdot S^{-1}$ of the matrix F and the diagonal form $\Lambda$ thereof, forming matrices $U_1 \cdot \Sigma_1^{1/2} \cdot S$ and $S^{-1} \cdot \Sigma_1^{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \cdot \\ \cdot \\ \cdot \\ V_L^T \end{bmatrix} \text{ and } S^{-1} \cdot \Sigma_1^{1/2} \cdot V_1^H = [W_1\ W_2\ W_3 \ldots W_{N-L+1}]$$

(h) the matrices $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} \text{ and } [W_1\ \Lambda^{-1} \cdot W_2\ \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} \text{; and}$$

and (i) calculating a matrix C of complex amplitudes according to the relationship $C = \mathrm{diag}\{h_1, h_2, \ldots, h_p\} \cdot X_D$, whereby $h^T = (h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix}$$

and $X_D$ indicates the average value of the block matrices in $$[W_1 \Lambda^{-1} \cdot W_2 \Lambda^{-2} \cdot W_3 \ldots \Lambda^{-(N-L)} \cdot W_{N-L+1}].$$

3. A method as claimed in claim 1 wherein step (f) comprises identifying the matrix F by a method of least error squares.

4. A method as claimed in claim 1 wherein step (f) comprises identifying the matrix F by a method of total least squares.

5. A method as claimed in claim 1 wherein the step of identifying the location in said patient of a source of selected parts of said cardiac sequences $y_i(n)$ comprises identifying pathological regions in the heart muscle of said patient which cause late potentials in said cardiac sequences $y_i(n)$.

6. A method as claimed in claim 1 comprising the additional step of generating a histogram of said frequencies.

7. A method as claimed in claim 2 comprising the additional step of generating a synthetic signal for visualizing harmonic components in said cardiac sequences $y_i(n)$ by in-phase superimposition.

8. A method for high-resolution spectral analysis of electrical cardiac signals comprising the steps of:

(a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ in said plurality i of sensor channels with $1 \leq i \leq M$ at times n with $0 \leq n \leq N-1$;

(b) combining said cardiac sequences $y_i(n)$ to form a data vector and transposing said data vector to obtain $$y(n)=[(y_1(n), \ldots, y_m(n)]^T$$

(c) combining a plurality of data vectors $y_n$ to form a matrix $$Y_T = \begin{bmatrix} y(0) & y(1) & \ldots & y(N-L) \\ y(1) & y(2) & \ldots & y(N-L+1) \\ \cdot & \cdot & & \cdot \\ \cdot & \cdot & & \cdot \\ y(L-1) & y(L) & \ldots & y(N-1) \end{bmatrix}$$

(d) implementing a singular value resolution $Y_T = U \cdot \Sigma \cdot V_H$ of the matrix $\gamma_E$ and the singular values are subjected to a threshold operation, as a result of which all singular values of $Y_T$ that are lower than the threshold in terms of amount are replaced by zero and all singular values of $Y_T$ not replaced by zero are contained in the block matrix $\Sigma_1$ of the resolution (e) identifying matrices $\theta_1$ and $\theta_2$ for which $$Y_T = [U_1\ U_2] \cdot \begin{bmatrix} \Sigma_1 & 0 \\ 0 & 0 \end{bmatrix} \cdot \begin{bmatrix} V_1^H \\ V_2^H \end{bmatrix}$$

$$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

whereby $\theta_1$ and $\theta_2$ respectively indicate the first and the last block matrix; and identifying a matrix F which is an optimum solution of the generally over-defined equation system $\theta_1 \cdot F = \theta_2$, wherein the imaginary parts of the natural logarithms of the eigenvalues of F are the soft, spectral frequencies of said cardiac sequences $y_i(n)$, and the real parts of the natural logarithms of the eigenvalues of F are attenuation constants associated with these frequencies, and identifying a location in said subject of a source of selected parts of said cardiac sequences $y_i(n)$ from said complex amplitude on the basis of said known spatial arrangement of said sensors.

9. A method as claimed in claim 8 comprising the additional steps of:

(g) from the similarity transformation $F = S \cdot \Lambda \cdot S^{-1}$ of the matrix F and the diagonal form $\Lambda$ thereof, forming matrices $U_1 \cdot \Sigma_1^{1/2} \cdot S$ and $S^{-1} \cdot \Sigma_1^{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \cdot \\ \cdot \\ \cdot \\ V_L^T \end{bmatrix} \text{ as well as}$$

$$S^{-1} \cdot \Sigma_1^{1/2} \cdot V_I^H = [W_1\ W_2\ W_3\ \ldots\ W_{N-L+1}]$$

(h) the matrices $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} \text{ and } [W_1\ \Lambda^{-1} \cdot W_2\ \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} \text{; and}$$

and (i) calculating a matrix C of complex amplitudes according to the relationship $C = \text{diag}\{h_1, h_2, \ldots, h_p\} \cdot X_D$, whereby $h^T = (h_1, h_2, \ldots, h_p)$ indicates tile average value of the row vectors of $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix}$$

and $X_D$ indicates the average value of the block matrices in $$[W_1 \Lambda^{-1} \cdot W_2 \Lambda^{-2} \cdot W_3 \ldots \Lambda^{-(N-L)} \cdot W_{N-L+1}].$$

10. A method as claimed in claim 8 wherein step (f) comprises identifying the matrix F by a method of least error squares.

11. A method as claimed in claim 8 wherein step (f) comprises identifying the matrix F by a method of total least squares.

12. A method as claimed in claim 8 wherein the step of identifying the location in said patient of a source of selected parts of said cardiac sequences $y_i(n)$ comprises identifying pathological regions in the heart muscle of said patient which cause late potentials in said cardiac sequences $y_i(n)$.

13. A method as claimed in claim 8 comprising the additional step of generating a histogram of said frequencies.

14. A method as claimed in claim 9 comprising the additional step of generating a synthetic signal for visualizing harmonic components in said cardiac sequences $y_i(n)$ by in-phase superimposition.

15. A method for high-resolution spectral analysis of electrical cardiac signals comprising the steps of:
   (a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ of in said plurality i of sensor channels with $1 \leq i \leq M$ at times n with $0 \leq n \leq N-1$;
   (b) combining said sequences $y_i(n)$ to form a data vector and transposing said data vector to obtain $$y(n)=[(y_1(n), \ldots, y_m(n))]^T$$

(c) combining a plurality of data vectors $y_n$ to form an expanded block-Hankel matrix
   (d) implementing a singular value resolution $\gamma_E = U \cdot \Sigma \cdot V_H$ of the matrix $\gamma_E$ and the singular values are subjected to a threshold operation, as a result of which all singular values of $\gamma_E$ that are lower than the threshold in terms of $$Y_E = \begin{bmatrix} y^T(0) & y^T(1) & \ldots & y^T(N-L) & y^H(0) & y^H(1) & \ldots & y^H(N-L) \\ y^T(1) & y^T(2) & \cdots & y^T(N-L+1) & y^H(1) & y^H(2) & \cdots & y^H(N-L+1) \\ \vdots & \vdots & & \vdots & \vdots & \vdots & & \vdots \\ y^T(L-1) & y^T(L) & \cdots & y^T(N-L) & y^H(L-1) & y^H(L) & \cdots & y^H(N-1) \end{bmatrix}$$

amount are replaced by zero and all singular values of $\gamma_E$ not replaced by zero are contained in the block matrix $\Sigma_1$ of the resolution $$Y_E = [U_1\ U_2] \cdot \begin{bmatrix} \Sigma_1 & 0 \\ 0 & 0 \end{bmatrix} \cdot \begin{bmatrix} V_1^H \\ V_2^H \end{bmatrix}$$

(e) identifying matrices $\theta_1$ and $\theta_2$ for which $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

whereby $\theta_1$ and $\theta_2$ respectively indicate the first and the last block matrix; and
   (f) identifying a matrix F which is an optimum solution of the generally over-defined equation system $\theta_1 \cdot F = \theta_2$, wherein the imaginary parts of the natural logarithms of the eigenvalues of F are the soft, spectral frequencies of said cardiac sequences $y_1(n)$, and the real parts of the natural logarithms of the eigenvalues of F are attenuation constants associated with these frequencies, and identifying a location in said subject of a source of selected parts of said cardiac sequences $y_1(n)$ from said complex amplitude on the basis of said known spatial arrangement of said sensors.

16. A method as claimed in claim 15 comprising the additional steps of:
   (g) from the similarity transformation $F = S \cdot \Lambda \cdot S^{-1}$ of the matrix F and the diagonal form $\Lambda$ thereof, forming matrices $U_1 \cdot \Sigma_1^{1/2} \cdot S$ and $S^{-1} \cdot \Sigma_1^{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \vdots \\ V_L^T \end{bmatrix} \text{ and } S^{-1} \cdot \Sigma_1^{1/2} \cdot V_1^H = [W_1\ W_2\ W_3 \ldots W_{N-L+1}]$$

(h) the matrices $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} \text{ and } [W_1\ \Lambda^{-1} \cdot W_2\ \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} ; \text{and}$$

(i) calculating a matrix C of complex amplitudes according to the relationship $C = \text{diag}\{h_1, h_2, \ldots, h_p\} \cdot X_D$, whereby $h^T = (h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix}$$

and $X_D$ indicates the average value of the block matrices in $$[W_1 \Lambda^{-1} \cdot W_2 \Lambda^{-2} \cdot W_3 \ldots \Lambda^{-(N-L)} \cdot W_{N-L+1}].$$

17. A method as claimed in claim 15 wherein step (f) comprises identifying the matrix F by a method of least error squares.

18. A method as claimed in claim 15 wherein step (f) comprises identifying the matrix F by a method of total least squares.

19. A method as claimed in claim 15 wherein the step of identifying the location in said patient of a source of cardiac selected parts of said sequences $y_i(n)$ comprises identifying pathological regions in the heart muscle of said patient which cause late potentials in said cardiac sequences $y_i(n)$.

20. A method as claimed in claim 15 comprising the additional step of generating a histogram of said frequencies.

21. A method as claimed in claim 16 comprising the additional step of generating a synthetic signal for visualizing harmonic components in said cardiac sequences $y_i(n)$ by in-phase superimposition.

22. A method for high-resolution spectral analysis of electrical cardiac signals comprising the steps of:

(a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ in said plurality i of sensor channels with $1 \leq i \leq M$ at times n with $0 \leq n < N-1$;

(b) combining said cardiac sequences $y_i(n)$ to form a data vector and transposing said data vector to obtain $$y(n) = [(y_1(n), \ldots, y_m(n)]^T$$

(c) combining a plurality of data vectors $y_n$ to form a matrix $$Y_E = \begin{bmatrix} y^T(0) & y^T(1) & \ldots & y^T(N-L) \\ y^T(1) & y^T(2) & \cdots & y^T(N-L+1) \\ \cdot & \cdot & & \cdot \\ \cdot & \cdot & & \cdot \\ y^T(L-1) & y^T(L) & \cdots & y^T(N-1) \end{bmatrix}$$

(d) implementing a singular value resolution $\gamma_E = U \cdot \Sigma \cdot V_H$ of the matrix $\gamma_E$ and the singular values are subjected to a threshold operation, as a result of which all singular values of $\gamma_E$ that are lower than the threshold in terms of amount are replaced by zero and all singular values of $\gamma_E$ not replaced by zero are contained in the block matrix $\Sigma_1$ of the resolution $$Y_E = [U_1 \; U_2] \cdot \begin{bmatrix} \Sigma_1 & 0 \\ 0 & 0 \end{bmatrix} \cdot \begin{bmatrix} V_1^H \\ V_2^H \end{bmatrix}$$

(e) identifying matrices $\theta_1$ and $\theta_2$ for which $$U_1 \cdot \Sigma_1^{1/2} = \begin{bmatrix} \Theta_1 \\ \Theta_2 \end{bmatrix} = \begin{bmatrix} \theta_1 \\ \theta_2 \end{bmatrix}$$

whereby $\theta_1$ and $\theta_2$ respectively indicate the first and the last block matrix; and (f) identifying a matrix F which is an optimum solution of the generally over-defined equation system $\theta_1 \cdot F = \theta_2$, wherein the imaginary parts of the natural logarithms of the eigenvalues of F are the soft, spectral frequencies of said cardiac sequences $y_1(n)$, and the real parts of the natural logarithms of the eigenvalues of F are attenuation constants associated with these frequencies, and identifying ventricular late potentials from said imaginary and real parts of said eigenvalues of F.

23. A method as claimed in claim 22 wherein step (a) comprises obtaining said chronological electrical cardiac sequences $y_i(n)$ in a terminal portion of a QRS complex up to the ST waveform.

24. A method as claimed in claim 23 comprising the additional step, before step (b), of compensating for constant parts and linear trends in said cardiac sequences $y_i(n)$.

25. A method as claimed in claim 23 comprising the additional steps of:

(g) from the similarity transformation $F = S \cdot \Lambda \cdot S^{-1}$ of the matrix F and the diagonal form $\Lambda$ thereof, forming matrices $U_1 \cdot \Sigma_1^{1/2} \cdot S$ and $S^{-1} \cdot \Sigma_{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \cdot \\ \cdot \\ \cdot \\ V_L^T \end{bmatrix} \text{ and } S^{-1} \cdot \Sigma_1^{1/2} \cdot V_1^H = [W_1 \; W_2 \; W_3 \ldots W_{N-L+1}]$$

(h) the matrices $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} \text{ and } [W_1 \Lambda^{-1} \cdot W_2 \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix} ; \text{ and}$$

(i) calculating a matrix C of complex amplitudes according to the relationship $C = \text{diag}\{h_1, h_2, \ldots, h_p\} \cdot X_D$, whereby $h^T = (h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \cdot \\ \cdot \\ V_L^T \cdot \Lambda^{-(L-1)} \end{bmatrix}$$

and $X_D$ indicates the average value of the block matrices in $$[W_1 \Lambda^{-1} \cdot W_2 \Lambda^{-2} \cdot W_3 \ldots \Lambda^{-(N-L)} \cdot W_{N-L+1}].$$

26. A method as claimed in claim 25 comprising the additional step of generating a synthetic signal for visualizing harmonic components in said cardiac sequence $y_i(n)$ by in-phase superimposition.

27. A method as claimed in claim 22 wherein step (f) comprises identifying the matrix F by a method of least error squares.

28. A method as claimed in claim 22 wherein step (f) comprises identifying the matrix F by a method of total least squares.

29. A method as claimed in claim 22 comprising the additional step of generating a histogram of said frequencies.

30. A method for high-resolution spectral analysis of electrical cardiac signals comprising the steps of:

(a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ in said plurality i of sensor channels with $1 \leq i \leq M$ at times n with $0 \leq n \leq N-1$;

(b) combining said cardiac sequences $y_i(n)$ to form a data vector and transposing said data vector to obtain $$y(n) = [(y_1(n), \ldots, y_m(n)]^T$$

(c) combining a plurality of data vectors $y_n$ to form a matrix $$Y_T = \begin{bmatrix} y(0) & y(1) & \ldots & y(N-L) \\ y(1) & y(2) & \ldots & y(N-L+1) \\ \vdots & \vdots & & \vdots \\ y(L-1) & y(L) & \ldots & y(N-1) \end{bmatrix}$$

(d) implementing a singular value resolution $Y_T = U \cdot \Lambda \cdot V_H$ of the matrix $\gamma_E$ and the singular values are subjected to a threshold operation, as a result of which all singular values of $Y_T$ that are lower than the threshold in terms of amount are replaced by zero and all singular values of $Y_T$ not replaced by zero are, contained in the block matrix $\Lambda$ of the resolution $$Y_T = [U_1 \, U_2] \cdot \begin{bmatrix} \Sigma_1 & 0 \\ 0 & 0 \end{bmatrix} \cdot \begin{bmatrix} V_1^H \\ V_2^H \end{bmatrix}$$

(e) identifying matrices $\theta_1$ and $\theta_2$ for which $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

whereby $\theta_1$ and $\theta_2$ respectively indicate the first and the last block matrix; and (f) identifying a matrix F which is an optimum solution of the generally over-defined equation system $\theta_1 \cdot F = \theta_2$, wherein the imaginary parts of the natural logarithms of the eigenvalues of F are the soft, spectral frequencies of said cardiac sequences $y_i(n)$, and the real parts of the natural logarithms of the eigenvalues of F are attenuation constants associated with these frequencies, and identifying ventricular late potentials from said imaginary and real parts of said eigenvalues of F.

31. A method as claimed in claim 30 wherein step (a) comprises obtaining said chronological electrical cardiac sequences $y_i(n)$ in a terminal portion of a QRS complex up to the ST waveform.

32. A method as claimed in claim 31 comprising the additional step, before step (b), of compensating for constant parts and linear trends in said cardiac sequences $y_i(n)$.

33. A method as claimed in claim 30 comprising the additional steps of:

(g) from the similarity transformation $F = S \cdot \Lambda \cdot S^{-1}$ of the matrix F and the diagonal form $\Lambda$ thereof, forming matrices $U_1 \cdot \Sigma_1^{1/2} \cdot S$ and $S^{-1} \cdot \Sigma_1^{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \vdots \\ V_L^T \end{bmatrix} \text{ and } S^{-1} \cdot \Sigma_1^{1/2} \cdot V_1^H = [W_1 \, W_2 \, W_3 \ldots W_{N-L+1}]$$

(h) the matrices $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} \text{ and } [W_1 \, \Lambda^{-1} \cdot W_2 \, \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} ; \text{ and}$$

(i) calculating a matrix C of complex amplitudes according to the relationship $C = \text{diag}\{h_1, h_2, \ldots, h_p\} \cdot X_D$, whereby $h^T = (h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix}$$

and $X_D$ indicates the average value of the block matrices in $$[W_1 \, \Lambda^{-1} \cdot W_2 \, \Lambda^{-2} \cdot W_3 \ldots \Lambda^{-(N-L)} \cdot W_{N-L+1}].$$

34. A method as claimed in claim 33 comprising the additional step of generating a synthetic signal for visualizing harmonic components in said cardiac sequence $y_i(n)$ by in-phase superimposition.

35. A method as claimed in claim 30 wherein step (f) comprises identifying the matrix F by a method of least error squares.

36. A method as claimed in claim 30 wherein step (f) comprises identifying the matrix F by a method of total least squares.

37. A method as claimed in claim 30 comprising the additional step of generating a histogram of said frequencies.

38. A method for high-resolution spectral analysis of electrical cardiac signals comprising the steps of:

(a) placing a plurality of individual sensors of a cardiac signal measuring system in a known spatial relationship on a subject, respectively connecting said plurality of sensors to a plurality of sensor channels of said cardiac signal measuring system, and obtaining M chronological electrical cardiac sequences $y_i(n)$ of in said plurality i of sensor channels with $1 \leq i \leq M$ at times n with $0 \leq n < N-1$;

(b) combining said sequences $y_i(n)$ to form a data vector and transposing said data vector to obtain $$y(n) = [(y_1(n), \ldots, y_m(n)]^T$$

(c) combining a plurality of data vectors $y_n$ to form an expanded block-Hankel matrix $$Y_E = \begin{bmatrix} y^T(0) & y^T(1) & \ldots & y^T(N-L) & y^H(0) & y^H(1) & \ldots & y^H(N-L) \\ y^T(1) & y^T(2) & \cdots & y^T(N-L+1) & y^H(1) & y^H(2) & \cdots & y^H(N-L+1) \\ \vdots & \vdots & & \vdots & \vdots & \vdots & & \vdots \\ y^T(L-1) & y^T(L) & \cdots & y^T(N-L) & y^H(L-1) & y^H(L) & \cdots & y^H(N-1) \end{bmatrix}$$

(d) implementing a singular value resolution $\gamma_E = U \cdot \Sigma \cdot V_H$ of the matrix $\gamma_E$ and the singular values are subjected to a threshold operation, as a result of which all singular values of $\gamma_E$ that are lower than the threshold in terms of amount are replaced by zero and all singular values of $\gamma_E$ not replaced by zero are contained in the block matrix $\Sigma_1$ of the resolution $$Y_E = [U_1\ U_2] \cdot \begin{bmatrix} \Sigma_1 & 0 \\ 0 & 0 \end{bmatrix} \cdot \begin{bmatrix} V_1^H \\ V_2^H \end{bmatrix}$$

(e) identifying matrices $\theta_1$ and $\theta_2$ for which $$U_1 \cdot \Sigma_1^{1/2} = \begin{bmatrix} \Theta_1 \\ \theta_2 \end{bmatrix} = \begin{bmatrix} \theta_1 \\ \Theta_2 \end{bmatrix}$$

whereby $\theta_1$ and $\theta_2$ respectively indicate the first and the last block matrix; and (f) identifying a matrix F which is an optimum solution of the generally over-defined equation system $\theta_1 \cdot F = \theta\theta_2$, wherein the imaginary parts of the natural logarithms of the eigenvalues of F are the soft, spectral frequencies of said cardiac sequences $y_1(n)$, and the real parts of the natural logarithms of the eigenvalues of F are attenuation constants associated with these frequencies, and identifying ventricular late potentials from said imaginary and real parts of said eigenvalues of F.

39. A method as claimed in claim 38 wherein step (a) comprises obtaining said chronological electrical cardiac sequences $y_i(n)$ in a terminal portion of a QRS complex up to the ST waveform.

40. A method as claimed in claim 39 comprising the additional step, before step (b), of compensating for constant parts and linear trends in said cardiac sequences $y_i(n)$.

41. A method as claimed in claim 38 comprising the additional steps of:

(g) from the similarity transformation $F = S \cdot \Lambda S^{-1}$ of the matrix F and the diagonal form $\Lambda$ thereof, forming matrices $U_1 \cdot \Sigma_1^{1/2} \cdot S$ and $S^{-1} \cdot \Sigma_1^{1/2} \cdot V_1^H$ and are subdividing these matrices into block matrices $$U_1 \cdot \Sigma_1^{1/2} \cdot S = \begin{bmatrix} V_1^T \\ V_2^T \\ V_3^T \\ \vdots \\ V_L^T \end{bmatrix} \text{ and } S^{-1} \cdot \Sigma_1^{1/2} \cdot V_1^H = [W_1\ W_2\ W_3 \ldots W_{N-L+1}]$$

(h) the matrices $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} \text{ and } [W_1\ \Lambda^{-1} \cdot W_2\ \Lambda^{-2} \cdot W_3 \ldots \Lambda^{-(N-L)} \cdot W_{N-L+1}]$$

from the matrices of step (g)

$$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix} \text{; and}$$

(i) calculating a matrix C of complex amplitudes according to the relationship $C = \text{diag}\{h_1, h_2, \ldots, h_p\} \cdot X_D$, whereby $h^T = (h_1, h_2, \ldots, h_p)$ indicates the average value of the row vectors of $$\begin{bmatrix} V_1^T \\ V_2^T \cdot \Lambda^{-1} \\ V_3^T \cdot \Lambda^{-2} \\ \vdots \\ V_L^T \cdot \Lambda^{-(L-1)} \end{bmatrix}$$

and $X_D$ indicates the average value of the block matrices in $$[W_1 \; \Lambda^{-1} \cdot W_2 \; \Lambda^{-2} \cdot W_3 \ldots \Lambda^{-(N-L)} \cdot W_{N-L+1}].$$

42. A method as claimed in claim 38 wherein step (f) comprises identifying the matrix F by a method of least error squares.

43. A method as claimed in claim 38 wherein step (f) comprises identifying the matrix F by a method of total least squares.

44. A method as claimed in claim 41 comprising the additional step of generating a synthetic signal for visualizing harmonic components in said cardiac sequence $y_i(n)$ by in-phase superimposition.

45. A method as claimed in claim 38 comprising the additional step of generating a histogram of said frequencies.

* * * * *